United States Patent
Spann et al.

(10) Patent No.: US 8,378,323 B1
(45) Date of Patent: Feb. 19, 2013

(54) STERILIZING TOYBOX APPARATUS

(76) Inventors: Robert L. Spann, Ladson, SC (US);
Alfreda B. Spann, Ladson, SC (US)

( * ) Notice: Subject to any disclaimer, the term of this patent is extended or adjusted under 35 U.S.C. 154(b) by 490 days.

(21) Appl. No.: 12/560,566

(22) Filed: Sep. 16, 2009

(51) Int. Cl.
*A61L 9/20* (2006.01)

(52) U.S. Cl. ............. 250/504 R; 250/491.1; 250/493.1; 250/494.1; 250/496.1; 250/455.11; 422/1; 422/22; 422/24

(58) Field of Classification Search ............... 250/492.1, 250/493.1, 494.1, 496.1, 503.1, 504 R, 455.11; 422/1, 22, 24

See application file for complete search history.

(56) References Cited

U.S. PATENT DOCUMENTS

| | | | |
|---|---|---|---|
| D251,040 S | | 2/1979 | Pawlak |
| 5,120,499 A | * | 6/1992 | Baron .............................. 422/24 |
| 5,166,528 A | * | 11/1992 | Le Vay ..................... 250/455.11 |
| 6,753,536 B2 | * | 6/2004 | Humphreys et al. ...... 250/455.11 |
| 2004/0118427 A1 | * | 6/2004 | Palfy et al. ........................ 134/1 |
| 2005/0220665 A1 | * | 10/2005 | Ding ................................ 422/20 |
| 2008/0118395 A1 | * | 5/2008 | Benedek ........................... 422/4 |
| 2009/0185960 A1 | * | 7/2009 | Busujima ...................... 422/116 |
| 2009/0227008 A1 | * | 9/2009 | Busujima ................... 435/289.1 |

* cited by examiner

*Primary Examiner* — Michael Logie

(57) ABSTRACT

The sterilizing toybox apparatus addresses illness risk, especially with children, by providing UV light sterilization within. UV lighting is offered both above and beyond toys within the apparatus. A time-release latch ensures exposure for a time determined to be optimal for UV exposure of contents. The apparatus provides UV lighting both in the bottom of the chest and in the lid. The clear shelf above the lower UV bulbs is in communication with the vibrator that jostles any toys so that full UV exposure is ensured. Reflective material distributed fully within the chest further guarantees full exposure of contents to sterilization. Additionally, the optional mesh basket is selectively suspended within the chest.

12 Claims, 6 Drawing Sheets

STERILIZING TOYBOX APPARATUS

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

The effectiveness of ultraviolet light, best known as UV, has been well established with regard to sterilization. UV is quite effective against bacterial and against viral contamination. While UV has therefore been used to combat such demons in many realms, UV has not previously been employed to aid illness prevention with regard to children. Perhaps one item remains foremost in child contact, in a multi-child environment, and that item is the toybox. To that end, the present apparatus provides UV sanitation for toys within a timed latch equipped toybox.

FIELD OF THE INVENTION

The sterilizing toybox apparatus relates to toyboxes and more especially to a toybox providing UV sterilization for toys within.

SUMMARY OF THE INVENTION

The general purpose of the sterilizing toybox apparatus, described subsequently in greater detail, is to provide a sterilizing toybox apparatus which has many novel features that result in an improved sterilizing toybox apparatus which is not anticipated, rendered obvious, suggested, or even implied by prior art, either alone or in combination thereof.

To attain this, the sterilizing toybox apparatus addresses illness risk, especially with children, by providing UV light sterilization within. While the apparatus is not limited to toybox applications only, the advantages offered by toy sterilization are significant concerns in the designs of the various embodiments provided. UV lighting is offered both above and beyond toys within the apparatus. Additionally, the most complete embodiment provides a time-release latch that ensures exposure for a time determined to be optimal for UV exposure of contents. That time can vary selectively but is, at minimum, seven minutes. Upon latching the apparatus, the latch will not release until the minimum time has expired. Even in less complete embodiments, the apparatus still provides UV lighting both in the bottom of the chest and in the lid. Other features further ensure toy exposure to UV. The clear shelf above the lower UV bulbs is in communication with the vibrator that jostles any toys so that full UV exposure is ensured. Reflective material distributed fully within the chest further guarantees full exposure of contents to sterilization. Additionally, the optional mesh basket is selectively suspended within the chest. The mesh basket is ideal for exposing such toys as small cars to the UV light. The lid is not restricted to the arched lid and the castle illustrated herein but may be provided in a myriad of designs to further entice child use.

Thus has been broadly outlined the more important features of the improved sterilizing toybox apparatus so that the detailed description thereof that follows may be better understood and in order that the present contribution to the art may be better appreciated.

An object of the sterilizing toybox apparatus is to prevent the spread of illnesses by sterilization of disease carrying items.

Another object of the sterilizing toybox apparatus is to provide timed exposure of items to sterilizing UV light.

A further object of the sterilizing toybox apparatus is to prevent premature opening of the box to ensure that items within are properly sterilized.

An added object of the sterilizing toybox apparatus is to ensure full exposure of items within the apparatus to UV.

And, an object of the sterilizing toybox apparatus is to provide more than one layer of exposure within the apparatus.

Still another object of the apparatus is to be attractive.

These together with additional objects, features and advantages of the improved sterilizing toybox apparatus will be readily apparent to those of ordinary skill in the art upon reading the following detailed description of presently preferred, but nonetheless illustrative, embodiments of the improved sterilizing toybox apparatus when taken in conjunction with the accompanying drawings.

In this respect, before explaining the current embodiments of the improved sterilizing toybox apparatus in detail, it is to be understood that the sterilizing toybox apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved sterilizing toybox apparatus. It is therefore important that the claims be regarded as including such equivalent constructions insofar as they do not depart from the spirit and scope of the sterilizing toybox apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 6 thereof, the principles and concepts of the sterilizing toybox apparatus generally designated by the reference number 10 will be described.

Figure 1:
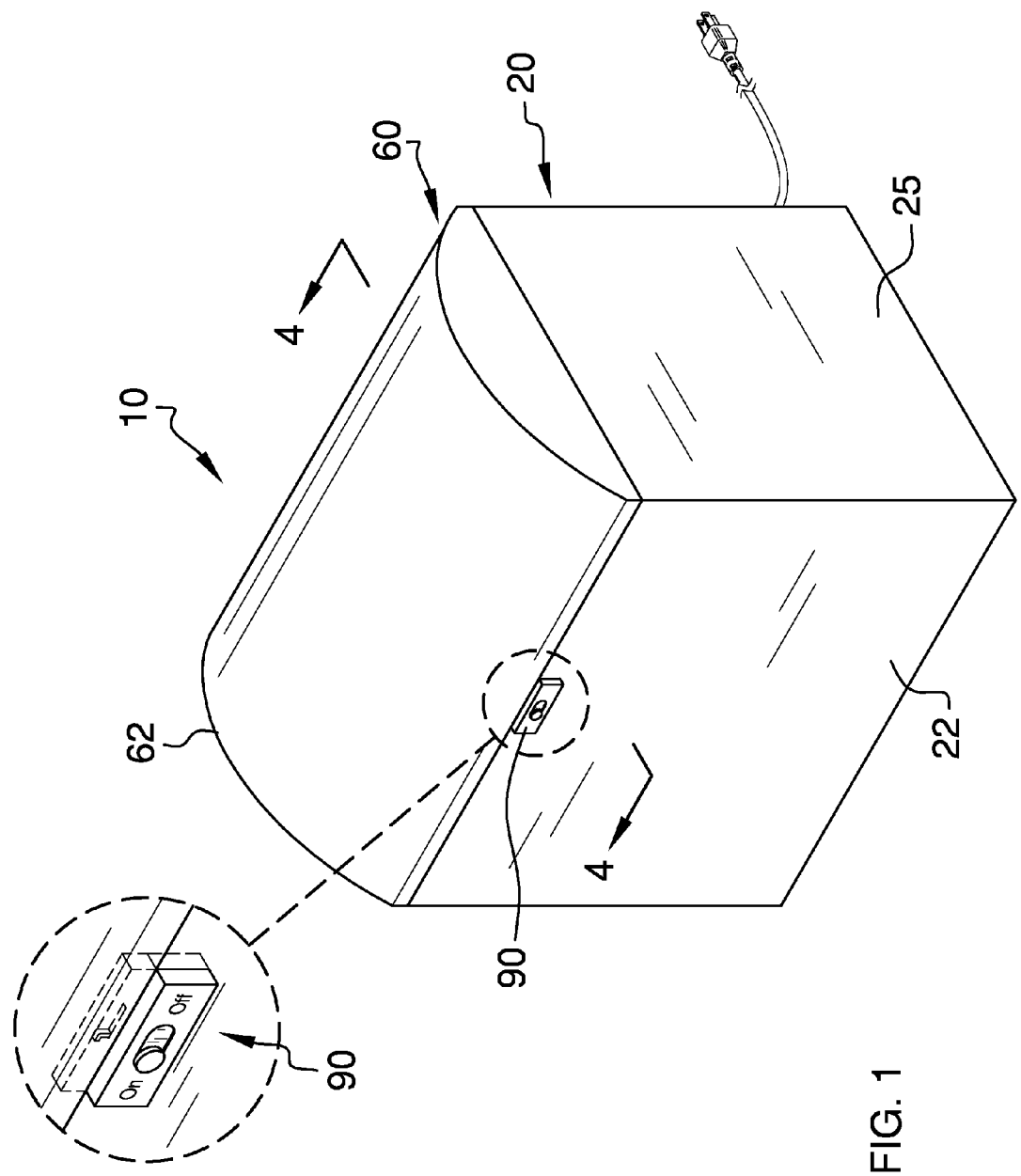
FIG. 1 is a perspective view, hinged lid with arch closed.
Figure 2:
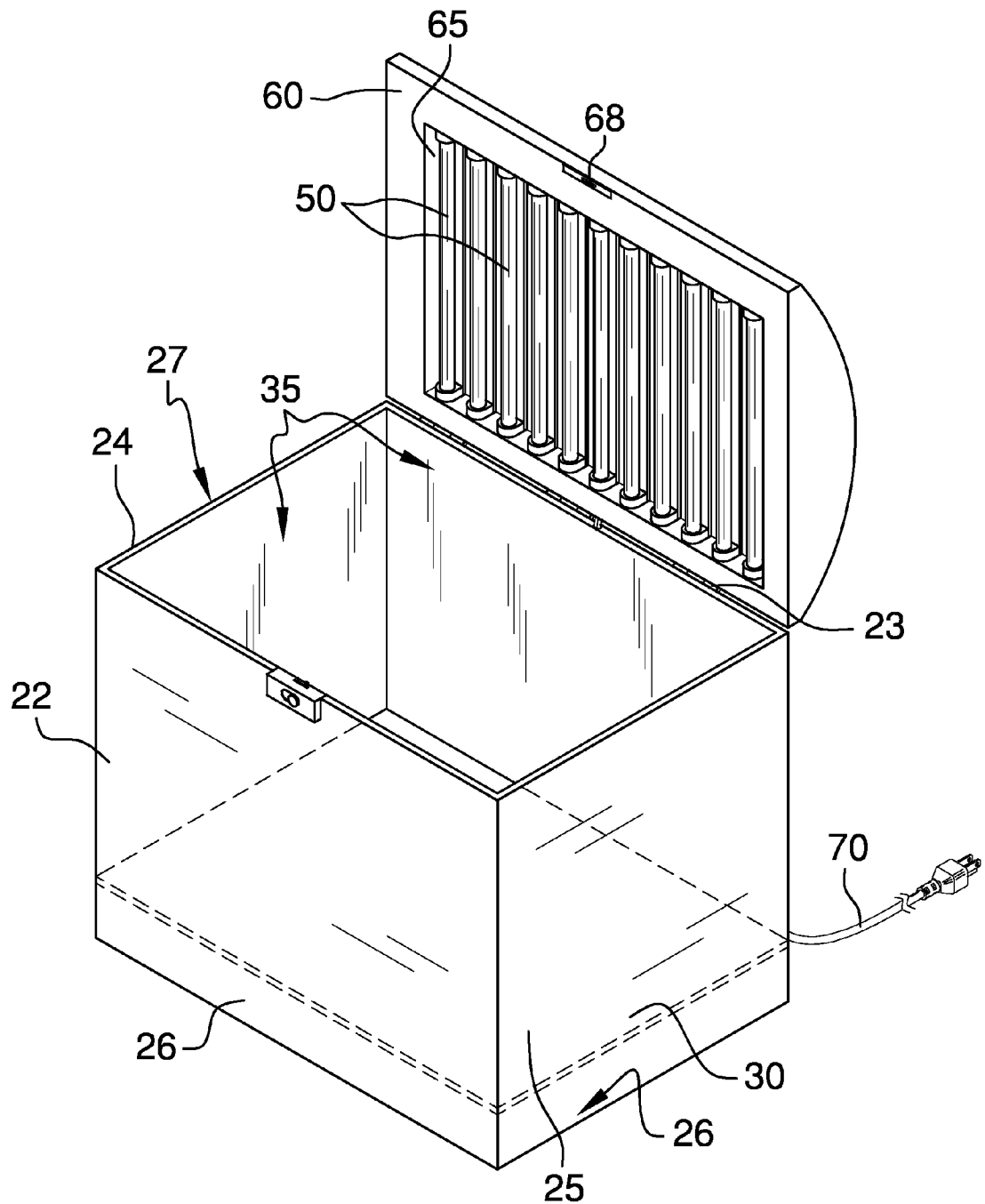
FIG. 2 is a perspective view, lid open.

Referring to FIGS. 1 and 2, the apparatus 10 partially comprises the rectangular chest 20 having a front 22 spaced apart from the back 23, a first side 24 spaced apart from the second side 25, and a bottom 26 spaced apart from the open top 27. Reflective material 35 is disposed within the chest 20 on the front 22, the back 23, the first side 24, the second side 25, and the bottom 26.

Figure 3:
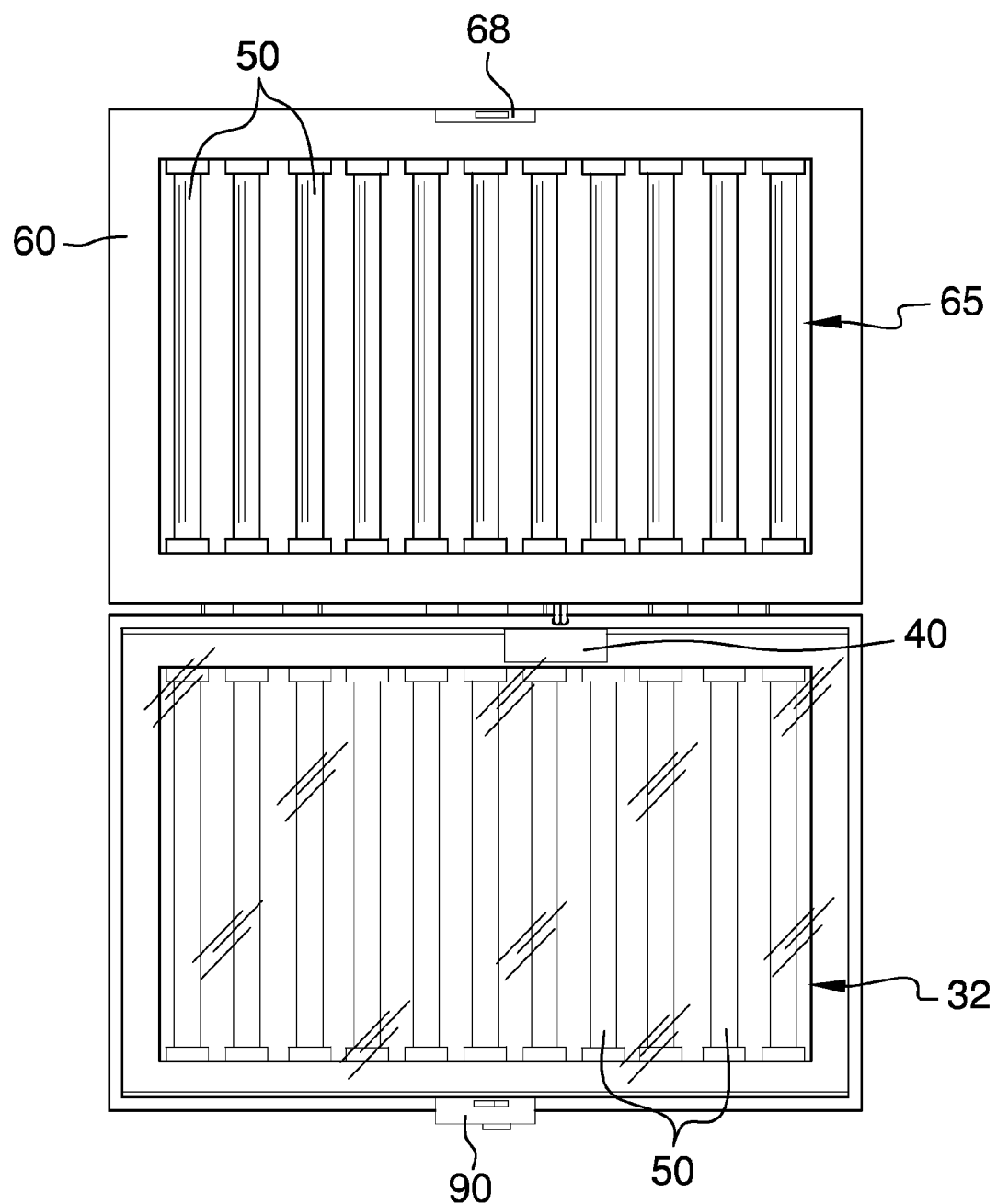
FIG. 3 is a top plan view, lid open.
Figure 4:
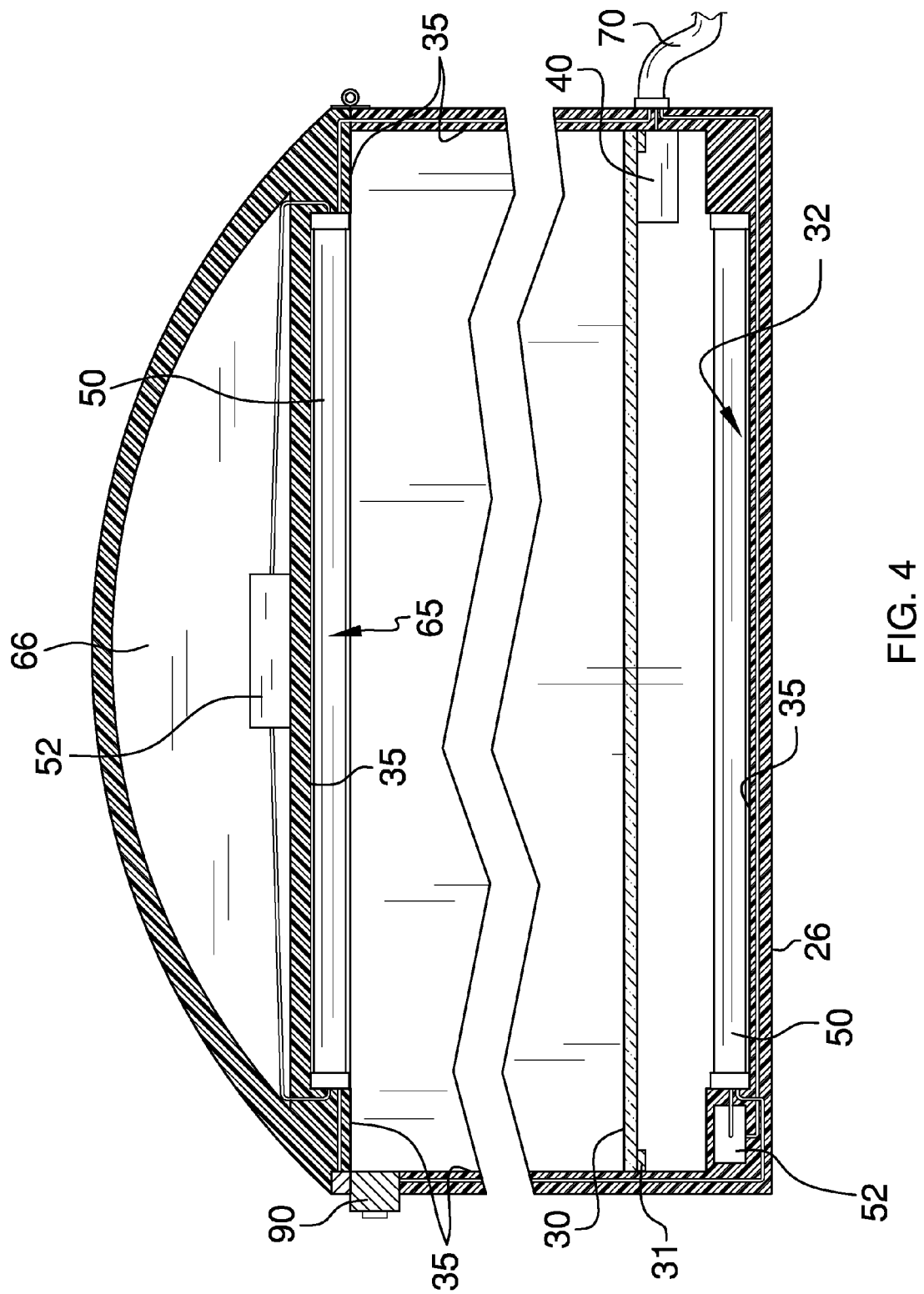
FIG. 4 is a lateral cross sectional view of FIG. 1, taken along the line 4-4.

Referring to FIGS. 3 and 4, the recession 32 comprises the majority of the bottom 26. A plurality of UV bulbs 50 is removably disposed within the recession 32. The UV bulbs 50 are disposed front 22 to back 23. The plurality of shelf supports 31 is disposed within the chest 20. The shelf supports 31 are disposed above and proximal to the recession 32. The vibrator 40 is mounted to the back 23 within the chest 20. The clear shelf 30 is removably disposed on the shelf supports 31. The shelf 30 is in contact with the vibrator 40 such that any items on the shelf are gently shaken and tossed to ensure full exposure to UV from the UV bulbs 50.

Figure 6:
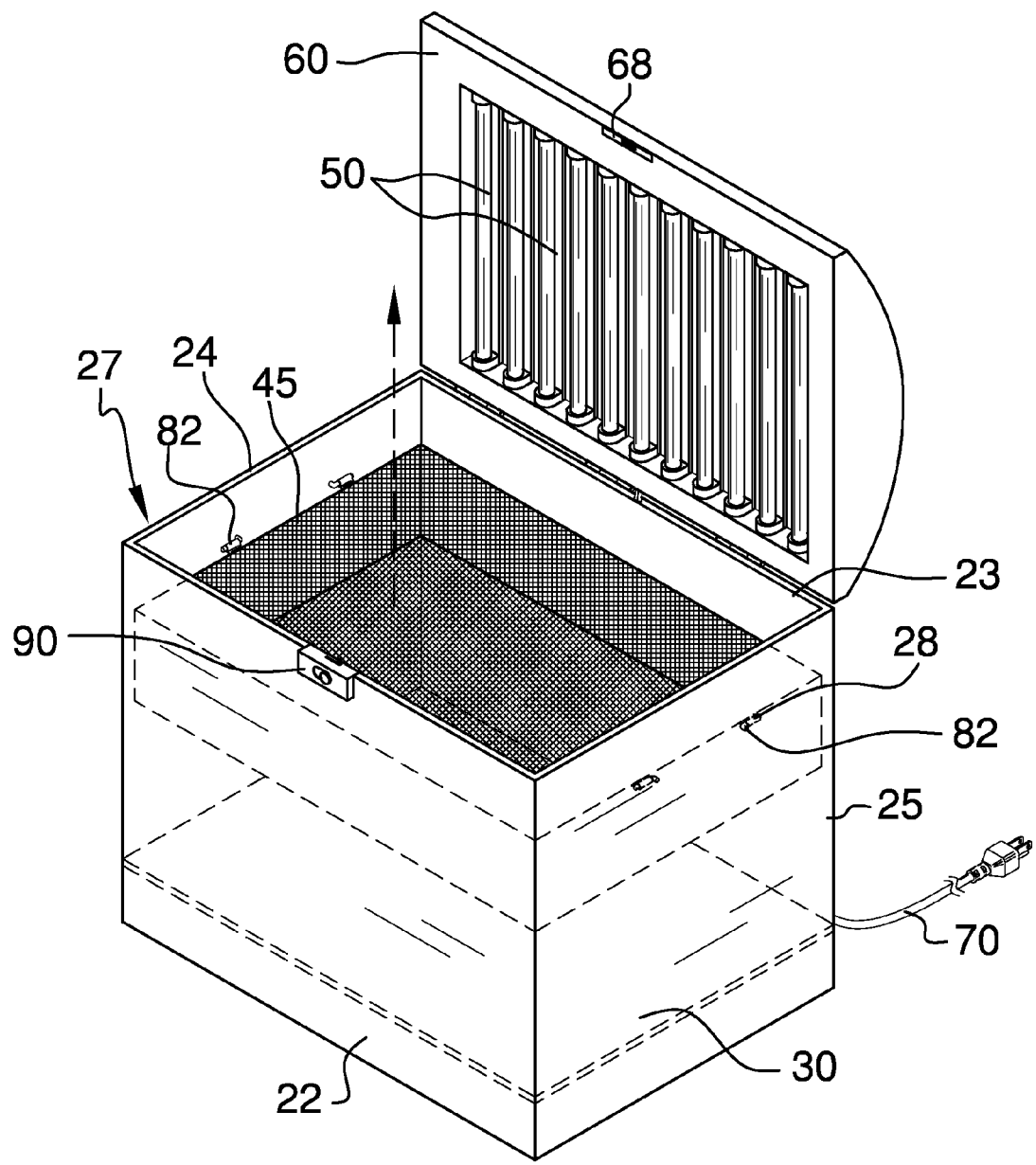
FIG. 6 is a perspective view with optional mesh basket.

Referring to FIG. 6, the plurality of loops 28 is disposed within the chest 20 on the first side 24 and second side 25. The loops 28 are disposed proximal to the open top 27. The mesh basket 45 is removably disposed within the chest 20. The mesh basket 45 is removably retained by a plurality of attached hooks 82 matching the plurality of loops 28 disposed within the chest 20. The sliding timed latch 90 is centrally disposed within the chest 20 front 22 adjacent to open top 27.

Figure 5:
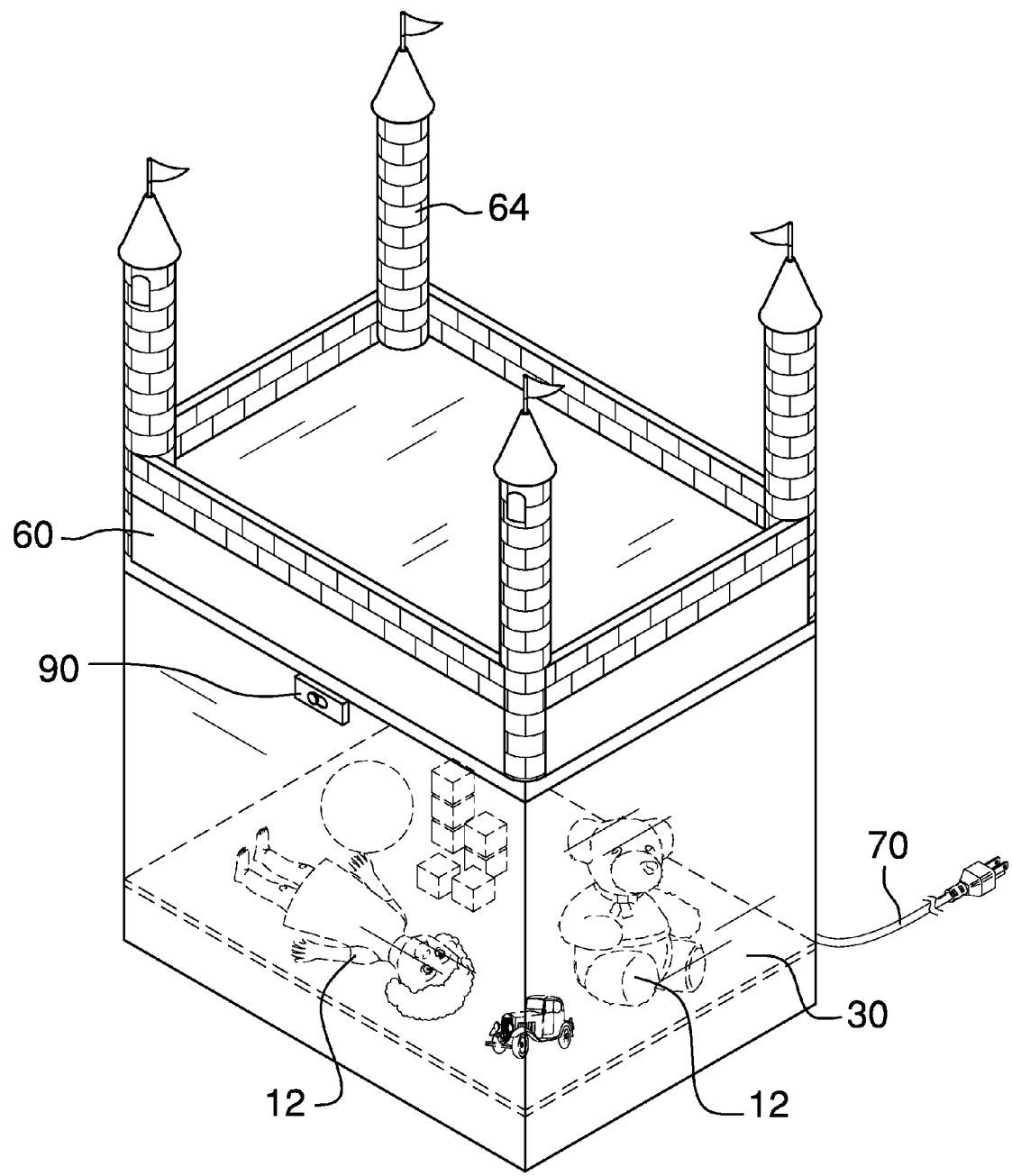
FIG. 5 is a perspective view with alternate castle hinged lid.

Referring to FIGS. 4 and 5, the hinged lid 60 is disposed on the chest 20. The latch receptacle 68 is disposed within the lid 60. The receptacle 68 is in receipt of the sliding latch 90. The latch 90 can be time-set such that once latched, the latch 90 does not release for at least 7 minutes. This ensures sterilization of all items, such as existing toys 12, prior to release.

Referring to FIGS. 2, 4, and 6, the lid recession 65 is disposed within a majority of the lid 60. A plurality of UV bulbs 50 is removably disposed within the lid recession 65. The cavity 66 is disposed within the lid 60. The cavity 66 contains one removably disposed ballast 52. The additional ballast 52 is removably housed adjacent to the chest 20 bottom 26 recession 32. Ballasts 52 are in communication with the UV bulbs 50. The power source 70 is fed through the chest 20 back 23 and is in communication with the ballasts 52, the latch 90, and the vibrator 40.

Referring to FIG. 5, the optional castle 64 hinged lid 60 is provided as an entertaining alternative embodiment to the arch 62 lid 60 of FIGS. 1-4 and 6.

With respect to the above description then, it is to be realized that the optimum dimensional relationships for the parts of the sterilizing toybox apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the sterilizing toybox apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the sterilizing toybox apparatus may be used.

Therefore, the foregoing is considered as illustrative only of the principles of the sterilizing toybox apparatus. Further, since numerous modifications and changes will readily occur to those skilled in the art, it is not desired to limit the sterilizing toybox apparatus to the exact construction and operation shown and described, and accordingly, all suitable modifications and equivalents may be resorted to, falling within the scope of the sterilizing toybox apparatus.

What is claimed is:

1. A sterilizing toybox apparatus, comprising, in combination:
   a rectangular chest having a front spaced apart from a back, a first side spaced apart from a second side, a bottom spaced apart from an open top;
   a recession comprising a majority of the bottom;
   a plurality of UV bulbs removably disposed within the recession, the UV bulbs disposed front to back;
   a ballast disposed adjacent to and in communication with the UV bulbs in the recession;
   a plurality of shelf supports disposed within the chest, the shelf supports disposed above and proximal to the recession;
   a vibrator mounted to the back within the chest;
   a clear shelf removably disposed on the shelf supports, the shelf in contact with the vibrator;
   a sliding latch centrally disposed within the chest front adjacent to the open top;
   a hinged lid disposed on the chest;
   a latch receptacle disposed within the lid, the receptacle in receipt of the chest sliding latch;
   a lid recession disposed within a majority of the lid;
   a cavity disposed within the lid;
   a plurality of UV bulbs removably disposed within the lid recession;
   a ballast disposed within the cavity, the ballast in communication with the lid recession UV bulbs;
   a power source disposed through the chest back, the power source in communication with both of the ballasts, the latch, and the vibrator.

2. The apparatus according to claim 1 further comprising a reflective material disposed within the chest.

3. The apparatus according to claim 2 wherein the reflective material is further disposed on the front, the back, the first side, the second side, the bottom, and an interior of the lid.

4. The apparatus according to claim 3 wherein the lid further comprises an arch.

5. The apparatus according to claim 3 wherein the lid further comprises a castle.

6. The apparatus according to claim 2 wherein the lid further comprises an arch.

7. The apparatus according to claim 2 wherein the lid further comprises a castle.

8. The apparatus according to claim 1 wherein the lid further comprises an arch.

9. The apparatus according to claim 1 wherein the lid further comprises a castle.

10. A sterilizing toybox apparatus, comprising, in combination: a rectangular chest having a front spaced apart from a back, a first side spaced apart from a second side, a bottom spaced apart from an open top; a reflective material disposed within the chest on the front, back, first side, second side, and the bottom; a recession comprising a majority of the bottom; a plurality of UV bulbs removably disposed within the recession, the UV bulbs disposed front to back; a ballast disposed adjacent to and in communication with the UV bulbs in the recession; a plurality of shelf supports disposed within the chest, the shelf supports disposed above and proximal to the recession; a vibrator mounted to the back within the chest; a clear shelf removably disposed on the shelf supports, the shelf in contact with the vibrator; a plurality of loops disposed within the chest on the first side and second side, the loops disposed proximal to the open top; a mesh basket removably disposed within the chest, the mesh basket removably retained by a plurality of attached hooks matching the plurality of loops disposed within the chest; a sliding timed latch centrally disposed within the chest front adjacent to the open top, the latch releasing upon a set time elapse; a hinged lid disposed on the chest; a latch receptacle disposed within the lid, the receptacle in receipt of the chest sliding latch; a lid recession disposed within a majority of the lid; a cavity disposed within the lid; a plurality of UV bulbs removably disposed within the lid recession; a ballast disposed within the cavity, the ballast in communication with the lid recession UV bulbs; a power source disposed through the chest back, the power source in communication with both of the ballasts, the latch, and the vibrator.

11. The apparatus according to claim 10 wherein the lid further comprises an arch.

12. The apparatus according to claim 10 wherein the lid further comprises a castle.

* * * * *